United States Patent [19]

Yagi et al.

[11] Patent Number: 4,564,708

[45] Date of Patent: Jan. 14, 1986

[54] OPTICAL RESOLUTION OF THE RACEMIC MODIFICATION OF 2,2'-BIS(DIPHENYLPHOSPHINO)-1,1'-BINAPHTHYLDIOXIDE

[75] Inventors: Misao Yagi; Susumu Akutagawa, both of Kanagawa, Japan

[73] Assignee: Takasago Perfumery Co., Ltd., Tokyo, Japan

[21] Appl. No.: 582,710

[22] Filed: Feb. 23, 1984

[30] Foreign Application Priority Data

Feb. 28, 1983 [JP]  Japan .................................. 58-30799

[51] Int. Cl.[4] ............................................. C07F 9/53
[52] U.S. Cl. ...................................................... 568/14
[58] Field of Search ......................................... 568/14

[56] References Cited

U.S. PATENT DOCUMENTS

| | | | |
|---|---|---|---|
| 2,642,461 | 6/1953 | Morris et al. | 568/14 |
| 3,075,017 | 1/1963 | Maier | 568/14 |
| 3,113,973 | 12/1963 | Hoffmann et al. | 568/14 |
| 3,145,227 | 8/1964 | Grayson et al. | 568/14 X |
| 3,458,581 | 7/1969 | Wu | 568/14 |
| 3,532,774 | 10/1970 | Maier | 568/14 X |
| 3,760,000 | 9/1973 | Curry | 568/14 |
| 3,780,112 | 12/1973 | Weinberg et al. | 568/14 |
| 4,376,870 | 3/1983 | Christopfel et al. | 568/14 X |

OTHER PUBLICATIONS

Chan et al., J. Org. Chem. 39 (12), 1748–1752 (1974).
Meisenheimer et al., Chem. Ber. 44, 356 (1911).
Meisenheimer et al., Ann. 449, 213–248 (1926).

Primary Examiner—Helen M. S. Sneed
Attorney, Agent, or Firm—Oblon, Fisher, Spivak, McClelland & Maier

[57] ABSTRACT

D-2,2'-bis(diphenylphosphino)-1,1'-binaphthyldioxide and l-2,2'-bis(diphenylphosphino)-1,1'-binaphthyldioxide are produced by reacting dl-2,2'-bis(diphenylphosphino)-1,1'-binapthyldioxide with optically active camphor-10-sulfonic acid or optically active 3-bromo-camphor-10-sulfonic acid as a resolving agent in a lower alkyl ester of acetic acid containing a lower alkyl carboxylic acid, thereby forming diastereomeric salts, and optically resolving said diastereomeric salts.

4 Claims, No Drawings

OPTICAL RESOLUTION OF THE RACEMIC MODIFICATION OF 2,2'-BIS(DIPHENYLPHOSPHINO)-1,1'-BINAPHTHYLDIOXIDE

BACKGROUND OF THE INVENTION

1. Field of the Invention

The present invention relates to a process for resolving dl-2,2'-bis(diphenylphosphino)-1,1'-binaphthyldioxide (referred to as BINAPO hereinafter) into optical active isomers.

BINAPO is an intermediate compound for producing 2,2'-bis(diphenylphosphino)-1,1'-binaphthyl (referred to as BINAP hereinafter) having the axial chirality which is useful as a ligand of an asymmetric hydrogenation catalyst or asymmetric isomerization catalyst.

2. Description of the Prior Art

Asymmetric synthesis is a comparatively new technical field. There are only a few reports on the production of catalysts for asymmetric synthesis. The production of BINAP is disclosed only in Japanese Patent Laid-open No. 61937/1980.

BINAP as the ligand of a catalyst for asymmetric synthesis should be optically active. It is resolved into d-BINAP and l-BINAP by changing BINAP into a BINAP-palladium complex, obtaining the d-isomer from crystals and the l-isomer from the mother liquor, and decomposing the respective isomers by reduction with LiAlH$_4$. This process is disadvantageous in being long, having poor yields, and requiring auxiliaries. There are many problems to be solved before this process is suitable for use by industry.

The optical resolution of phosphine oxide was reported by Henri Brunner et al. [Chem. Ber. 114, 1137–1149 (1981)]. According to this report, bicyclo [2,2,1]-heptene-5-2,3-dibis(diphenylphosphorane oxide) is reacted with L-(1)-dibenzoyl-tartaric acid to give a diastereomer, which is difficult to dissolve, and which is subsequently hydrolized to give the l-isomer. Additionally, there was also reported by Meisenheimer et al. [Chem. Ber. 44, 356 (1911), Ann. 449, 213–248 (1926)] the process for producing an optically active phosphorus compound of

type from d-camphor-10-sulfonic acid (referred to as d-CSA hereinafter) or d-3-bromocamphor-10-sulfonic acid (referred to as d-BCSA hereinafter). The process requires a long time for crystallization and is very difficult to practice.

Therefore, a need continues to exist for a process for the optical resolution of dl-2,2'-bis(diphenylphosphino)-1,1-binaphthyldioxide which provides excellent yields of the d and l enantiomeric compounds and which can be readily carried out on an industrial scale.

SUMMARY OF THE INVENTION

Accordingly, it is an object of the present invention to provide a process for the optical resolution of dl-2,2'-bis(diphenylphosphino)-1,1-binaphthyldioxide (BINAPO) which provides excellent yields of d-2,2'-bis(diphenylphosphino)-1,1'-binaphthyldioxide and l-2,2'-bis(diphenylphosphino)-1,1'-binaphthyldioxide.

It is also an object of this invention to provide a process for the optical resolution of di-2,2'-bis(diphenylphosphino)-1,1'-binaphthyldioxide into the d and l enantiomers on an industrial scale.

Further, it is an object of the present invention to provide a process for the optical resolution of dl-2,2'-bis(diphenylphosphino)-1,1'-binaphthyldioxide without having to use expensive auxiliary equipment or chemicals.

According to the present invention, the foregoing and other objects are attained by providing a process for the optical resolution of dl-2,2'-bis(diphenylphosphino)-1,1'-binaphthyldioxide which involves reacting dl-2,2'-bis(diphenylphosphino)-1,1'-binaphthyldioxide with optically active camphor-10-sulfonic acid or 3-bromocamphor-10-sulfonic acid as resolving agents in a lower alkyl ester of acetic acid containing a lower alkyl carboxylic acid, thereby forming diastereomeric salts; and optically resolving said diastereomeric salts.

DETAILED DESCRIPTION OF THE INVENTION

BINAPO which is the starting material in this invention can be produced according to the process disclosed in Japanese Patent Laid-open No. 61937/1980. According to this process, bromine and 1,1'-bi-2-naphthol are reacted with each other, using triphenyl phosphine as a reaction auxiliary, to give 2,2'-dibromo-1,1'-binaphthyl, which is then reacted with chlorodiphenyl phosphine in the presence of t-butyl lithium to give BINAP. BINAPO is obtained by oxidizing BINAP with peracetic acid or hydrogen peroxide.

According to the present invention, any one of d-camphor-10-sulfonic acid (d-CSA), l-camphor-10-sulfonic acid (l-CSA), d-3-bromocamphor-10-sulfonic acid (d-BCSA) or l-3-bromocamphor-10-sulfonic acid (l-BCSA) can be used as the resolving agent. These resolving agents are well described in the published chemical literature. See for example *Stereochemistry of Carbon Compounds*, by E. Eliel (McGraw-Hill 1962), pages 51–53.

In accordance with the present process dl-BINAPO is reacted with a resolving agent in a solvent which is a lower alkyl ester of acetic acid containing a lower carboxylic acid which forms a hydrogen bond with phosphine oxide. The lower carboxylic acid may be added dropwise to the solution of lower alkyl ester of acetic acid. On reaction, there crystallizes out a diastereomeric salt composed of d-CSA and d-BINAPO, or a diastereomeric salt composed of l-CSA and l-BINAPO, or a diastereomeric salt composed of d-BCSA and d-BINAPO, or a diastereomeric salt composed of l-BCSA and l-BINAPO, which all have low solubility. The crystals separated from the liquid are hydrolyzed to give optically active BINAPO.

The reactants are charged in the following ratios based on BINAPO. Resolving agent: about 1 to 5 times by mole, preferably about 1 to 2 times by mole. Lower alkyl ester of acetic acid (e.g., methyl acetate, ethyl acetate, and propyl acetate): about 2 to 5 times by weight. Lower alkyl carboxylic acid (e.g., acetic acid, propionic acid, and butyric acid): about 1 to 20 times by mole.

dl-BINAPO is readily soluble in the solvent when stirred with heating.

The diastereomeric salts crystallize out when the solution is allowed to stand or cooled with stirring. The crystallizing temperature may be properly selected according to the solubility of the diastereomeric salt to be obtained.

The crystals are dissolved in an organic solvent; and water, and a dilute alkaline aqueous solution as occasion demands, are added to the solution of the organic solvent to hydrolyze the diastereomeric salt. On hydrolysis of the diastereomeric salt, optically active BINAPO crystallizes out from the solution. By separation of the crystals, there is obtained the desired product. The water layer remaining after hydrolysis is condensed to recover the resolving agent.

Water is added to the mother liquor left after filtration of the diastereomeric salt to decompose the diastereomer. The solvent layer is condensed to give BINAPO containing the other optically active BINAPO. It is used as a raw material for the other optically active BINAPO.

The present invention will be further illustrated by certain examples and references which are provided for purposes of illustration only and are not intended to limit the present invention.

In the examples, the melting point was measured by using a melting point measuring apparatus of heater block type (made by Kabushiki Kaisha Yanagimoto Seisakusho). The optical rotation was measured by using Model DIP-2 made by Nippon Bunko Kogyo K.K. d-CSA.H$_2$O and d-BCSA are commercial products available from Nakarai Kagaku Yakuhin K.K. l-CSA.H$_2$O and l-BCSA are commercial products available from Yamakawa Yakuhin Kogyo K.K. Acetic acid, propionic acid, methyl acetate, and ethyl acetate are of reagent-grade. BINAPO has a melting point of 300° to 304° C.

The resolution of the optically active BINAPO obtained in the examples was confirmed by liquid chromatography with an optically active column and by comparison with the dl-isomer.

The liquid chromatography apparatus is JASCOTRI-II (made by Nippon Bunko Kogyo K.K.) with UV-100-III (254 mm) detector and HS-50-2(30) (25×0.4 cm) column. The chromatography was performed under the following conditions. Mobile phase: methanol. Concentration: 1.21 mg/ml. Flow rate: 0.5 ml/min. Temperature: 15° C. d-BINAPO (Rt: 41.5 minutes). l-BINAPO (Rt: 79.5 minutes).

EXAMPLES

Into a 1-liter three-neck flask equipped with a thermometer, dropping funnel, and Dimroth condenser were charged 65.4 g (0.1 mol) of dl-BINAPO, 25 g of d-CSA.H$_2$O, and 271 ml of ethyl acetate. 90 ml of acetic acid was added slowly with heating under reflux to make a completely uniform solution. With stirring, the temperature was lowered slowly to 2°-3° C. over about 2 hours. Stirring was continued at this temperature for 30 minutes for crystallization. The crude crystals were separated off by vacuum filtration, followed by washing with 100 ml of ethyl acetate cooled to 2° to 3° C. The crystals were suspended in 390 ml of toluene. The suspension was heated to 80° C. and 30 ml of water was added for decomposition. After separation of water, this step was repeated three times. The toluene solution was condensed by heating to about 50 ml, followed by cooling to room temperature. 50 ml of hexane was added slowly to complete crystallization. The crystals were filtered off and air-dried to give 22.2 of d-BINAPO (67.9% yield).

$[\alpha]_D^{24} = +399$ (c: 0.5, benzene)

m.p.=262°-263° C.

The mother liquor left after separation of crude crystals was distilled under reduced pressure to remove the solvent. To the resulting solids was added 1.9 liters of toluene, followed by heating to 80° C. for dissolution. To the resulting solution was added 100 ml of water for decomposition. After separation of the water layer, the same step as above was repeated twice by adding 100 ml of water. The separated water layers were combined and then condensed to recover d-CSA.

The toluene solution was condensed to about 150 ml. To the condensed solution was added slowly 150 ml to hexane at room temperature, followed by standing at room temperature for 2 hours for crystallization. The crystals were filtered off and air-dried. Thus there was recovered 40.6 g of BINAPO.

$[\alpha]_D^{24} = -211.6$ (c: 0.5, 1 benzene)

The recovered BINAPO was a mixture composed of about 23.5% of d-isomer and about 76.5% of l-isomer.

EXAMPLE 2

Crude crystals were obtained in the same manner as in Example 1 except that a 500-ml flask was used and the reactants were 32.7 g (0.05 mol) of dl-(BINAPO, 12.5 g of l-CSA.H$_2$O, 135 ml of ethyl acetate, and 45 ml of propionic acid.

The crude crystals were washed with 50 ml of cold ethyl acetate (2° to 3° C.). To the crystals was added 200 ml of toluene. The toluene suspension was heated to 80° C. with stirring. 30 ml of water was added for decomposition. The toluene layer was washed twice with each 15 ml of water to separate l-CSA in the form of aqueous solution. The toluene layer was condensed to about 25 ml, followed by standing for cooling to room temperature. 50 ml of hexane was added slowly to cause crystals to separate out. The crystals were filtered off and air-dried. Thus there was obtained 11 g (67.3% yield) of l-BINAPO.

$[\alpha]_D^{24} = -400$ (c: 0.5, benzene)

m.p.=262°-263° C.

EXAMPLE 3

Into a 100-ml three-neck flask equipped with a thermometer and Dimroth condenser were charged 13.1 g (0.02 mol) of dl-BINAPO, 6.23 g of d-BCSA, 40 ml of ethyl acetate, and 5 ml of acetic acid. The rectants were heated with stirring to make a uniform solution. The solution was cooled to 20° C. over about 2 hours. The solution was kept at 20° C. for 30 minutes to cause crystals to separate out. To the resulting crude crystals were added 27.5 ml of ethyl acetate and 10 ml of acetic acid, followed by heating for dissolution. The solution was cooled to 25° C. over 2 hours. The solution was kept at 25° C. for 30 minutes cause crystals to separate out. To the resulting crystals were added 18 ml of ethyl acetate and 12 ml of acetic acid. The solution was kept at 27° C. for 30 minutes for recrystallization. There was obtained 7.7 g of crystals. The crystals were dissolved in 250 ml of toluene with heating. To the solution of 50° C. was added 20 ml of water for decomposition. This step was repeated three times. The toluene layer was condensed to about 10 ml, followed by standing at room temperature for about 30 minutes. 10 ml of hexane was added slowly to cause crystals to separate out. The crystals were filtered off and air-dried to give 4.78 g of d-BINAPO (73% yield).

$[\alpha]_D^{24} = +404$ (c: 0.5, benzene)

m.p. = 262°–263° C.

EXAMPLE 4

The same operation as in Example 3 was carried out by charging 13.1 g of dl-BINAPO, 6.23 g of l-BCSA, 40 ml of methyl acetate, and 5 ml of acetic acid, whereby there was obtained 7.1 g of crystals. By treating the crystals in the same manner as in Example 3, there was obtained 4.36 g of l-BINAPO (66.6% yield).

$[\alpha]_D^{24} = -401$ (c: 0.5, benzene)

m.p. = 262°–263° C.

The present invention now makes it possible to perform the optical resolution of dl-BINAPO with ease on an industrial scale and to obtain optically active isomers of BINAPO in a high yield and at a low cost.

Having now fully described this invention, it will apparent to one of ordinary skill in the art that many changes and modifications can be made thereto without departing from the spirit or scope of the invention as set forth herein.

What is claimed as new and is intended to be secured by Letters Patent is:

1. A process for the optical resolution of dl-2,2'-bis(diphenylphosphino)-1,1'-binaphthyldioxide which comprises reacting dl-2,2'-bis(diphenylphosphino)-1,1'-binaphthyldioxide with any one of the optically active resolving agents d-camphor-10-sulfonic acid, l-camphor-10-sulfonic acid, d-3-bromocamphor-10-sulfonic acid or l-3-bromocamphor-10-sulfonic acid in a lower alkyl ester of acetic acid containing a lower alkyl carboxylic acid, thereby forming diastereomeric salts; and resolving said diastereomeric salts to afford the optically active isomers, and wherein said resolving agents are used in the amount of about 1 to 5 moles per mole of dl-DINAPO, and said lower alkyl ester of acetic acid is used in the amount of about 2 to 5 times by weight of the amount of dl-DINAPO, and wherein said lower alkyl carboxylic acid is used in an amount of about 1 to 20 times by mole per mole of dl-DINAPO.

2. The process as claimed in claim 1, wherein said lower alkyl ester of acetic acid is methyl acetate, ethyl acetate and propyl acetate and said lower alkyl carboxylic acid is acetic acid, propionic acid and butyric acid.

3. The process as claimed in claim 1, wherein said resolving agents are used in the amount of about 1 to 2 moles per mole of dl-BINAPO.

4. The process as in claim 1, wherein said lower alkyl carboxylic acid is added dropwise to the solution of lower alkyl ester of acetic acid.

* * * * *